United States Patent [19]

Woelfel

[11] Patent Number: 4,654,005

[45] Date of Patent: Mar. 31, 1987

[54] LEAF GAGE AND WAFER

[75] Inventor: Julian B. Woelfel, Columbus, Ohio

[73] Assignee: Ohio State University, Columbus, Ohio

[21] Appl. No.: 742,760

[22] Filed: Jun. 10, 1985

[51] Int. Cl.$^4$ .............................................. A61C 19/04
[52] U.S. Cl. ...................................... 433/72; 433/71; 433/37; 433/39
[58] Field of Search ........................ 433/34, 70, 71, 72, 433/37, 39, 46; 33/511, 513, 514, 168 R

[56] References Cited

U.S. PATENT DOCUMENTS

| | | | |
|---|---|---|---|
| 1,778,293 | 10/1930 | Galasso | 433/37 |
| 2,183,624 | 12/1939 | Schwartz | 433/71 |
| 2,498,171 | 2/1950 | Michler | 33/168 R |
| 2,633,637 | 4/1953 | Lucia | 433/70 |
| 3,579,832 | 5/1971 | Cooper | 433/72 |
| 3,916,527 | 11/1975 | Linkow | 433/37 |

OTHER PUBLICATIONS

J. P. Long, "Locating Centric Relation with a Leaf Gauge", The Journal of Prosthetic Dentistry, vol. 29, No. 6, Jun. 1973.

E. H. Williamson et al., "Centric Relation: A Comparison of Muscle-Determined Position and Operator Guidance", Journal of Orthodontics, Feb. 1980.

W. E. Shankland et al., "The Fabrication and Use of a Leaf Gauge to Locate Centric Relation", The Ohio Dental Journal, Nov. 1983.

Advertisement for TEMREX ® Bite Relator.

*Primary Examiner*—John J. Wilson
*Assistant Examiner*—Andriene J. Lepiane
*Attorney, Agent, or Firm*—Emch, Schaffer, Schaub & Porcello Co.

[57] ABSTRACT

A dental apparatus for use in efficiently obtaining an accurate relationship of upper and lower jaws of a dental patient which includes a wafer and a leaf gage. The wafer is made of a substantially stable but vertically deformable material and has a generally dental arcuate shape. A slot extends through the wafer for receiving the leaf gage. The leaf gage is positionable within the slot of the wafer and thereafter placed within a patient's mouth in order to obtain an accurate centric relation record.

13 Claims, 13 Drawing Figures

LEAF GAGE AND WAFER

BACKGROUND OF THE INVENTION

The present invention is directed to an improved disposable leaf gage and bite relationship wafer. The leaf gage and wafer are designed to be easily customized to adapt to the variety of occlusal relationships exhibited by differing patients.

Dentists have used many methods and devices in an attempt to assure the precise location and recording of a patient's mandible. To accurately record the centric relation location of the mandible it is important that both condyles be seated in their most posterior, middle and superior position in the mandibular fossae. The accuracy achieved is highly dependent upon the individual dentist's familiarity with the methodology he choses to use, previous experience, manipulative skills, knowledge of physiology and anatomy, and on the succeeding laboratory procedures. As a result, no single method to assure the precise location and recording of a patient's mandible has become universally accepted. The most popular methods include needlepoint tracing devices; holding the tip of the tongue back in the soft palate; telling the patient to swallow while closing; having the patient pull the lower jaw back or "stick the upper jaw out"; having the patient relax the mandible and let the dentist manipulate it upwards and posteriorly; and, telling the patient to relax and close naturally. More precise but far less popular methods include using clutches and a pantographic recording of mandibular border movements; using an anterior acrylic resin jig (Lucia jig) to guide the lower incisor and mandible in an upward posterior direction; or using a narrow strip of soft metal, popsicle stick, a plastic leaf gage, or firm wax placed anteriorly to exert posterior guidance during closure. Other methods include the use of a functional chew-in, electromyographic recordings, myomoniter, Boos power points or the so called "True Centric" type devices.

Since neuromuscular relaxation is a prerequisite of a physiolgically sound and scientific methodology, ideally all patient's temporomandibular joints should be programmed through a course of wearing a plastic maxillary occlusal splint (bite plane) for a short interval of time or until the mandible has assumed a stable comfortable position prior to making a centric relation jaw registration. This is true whether the necessary dental treatment is an occlusal equilibration, construction of a fixed or removable partial denture, or an entire full mouth occlusal rehabilitation. The dentist determines the extent of occlusal discrepancies in symptom free (temporomandibular joint) patients by testing the existent error using a leaf gage. When a patient bites firmly on a leaf gage which has been inserted between the patient's incisors at the appropriate angle, the patient's condyles are seated in the most superior and comfortable posterior position. However, there are problems associated with the prior art leaf gages. For example, some prior art leaf gages are made of sheets of plastic material affixed at one end with a brad. These plastic leaf gages are not disposable. The plastic leaf gages are sterilized with alcohol and reused by the dentist on different patients. However, the attempts to sterilize the leaf gage between such uses do not effectively provide adequate insurance that any communicable diseases, or diseases such as Acquired Immune Deficiency Syndrome or infectious hepatitis, will not be transmitted from one patient to another. In addition, the prior art leaf gages are not calibrated, so that the dentist cannot easily determine the thickness of the leaf gage used or the distance the patient's mouth has been opened. Most prior art leaf gages are too wide for best anterior tripoding along with the two condyles. Also, if the dentist later determines that another centric relation record is necessary, there is no simple way for the dentist to be sure that the same thickness of leaf gage will again be inserted between the patient's incisors.

It is important that existing occlusal discrepancies be eliminated prior to or along with any relatively extensive restorative dental treatment (crowns, bridges, etc.). This is accomplished by mounting accurate diagnostic dental stone casts on an articulator using a face-bow and performing a verifiable centric relation record to determine the degree and location of the interfering cusps. A diagnostic equilibration is then done on the dental stone teeth casts attached to the dental articulator so that the final result can be analyzed prior to removing any enamel in the mouth. It is not always possible to eliminate centric relation prematurities with an occlusal equilibration; therefore, surgical intervention and/or orthodontic treatment may be necessary. Thus, decision on whether to equilibrate or not and the method for observing, recording and eliminating undesirable tooth interferences is dependent on precise and repeatable closures of the mandible in the centric relation arc.

In addition to the numerous methods for assuring that the patient's mandible is in the most retruded position, many materials and carrying media are advocated for recording and transfering this relationship to an articulator. Dental compound, plaster, zinc oxide-eugenol paste, polysulfide rubber, silicone rubber, polyether rubber, self-activating acrylic resin, dental cement and more than fifty varieties of wax have been used as checkbite materials. These materials are sometimes carried to the mouth with a jig, a metal or plastic frame holding a glass fiber mesh or polyethelene sheet, a fork, a clutch, a soft metal or wax sheet, or these materials are merely applied directly over the teeth or applied to the carrier with a cement spatula. These prior art devices are clumsy and cumbersome to use. Further these devices are bulky and uncomfortable to the patient and frequently provide barriers for accurate closure of the jaw in the terminal hinge position. For example, a prior art plastic frame device and a prior art wire frame device both have a relatively thick posterior edge or end portion curving around the last molars which interferes with the patient's ability to properly close the mouth. Other frames, such as metal frames are both too thick and rigid, contoured incorrectly and consequently, do not accurately record the patient's undesirable tooth interferences.

Therefore, there is a need for an apparatus which is flexible, accurate, inexpensive, disposable, and quickly customized to be adaptable to most patient's occlusal relationships. In addition, there is a further need for an apparatus that can be used as an aid in assuring the accurage mounting of dental casts.

SUMMARY OF THE INVENTION

The present invention is directed to a leaf gage and wafer. The wafer of the present invention is a thin anatomically-shaped wafer which is made of a stiff or rigid material which is capable of being bent or deformed. The wafer can be coated on both sides with a thin sheet of a plastic material, such as the product known under the trademark MYLAR. In the preferred embodiment, the wafer includes a plurality of apertures disposed along the wafer and extending through the wafer. The wafer also defines a slot for holding a narrow disposable leaf gage of an appropriate thickness. The leaf gage of the present invention is constructed of a plurality of leaves, affixed at one end to form a booklet. A portion of the leaf gage booklet is selected by the dentist and is inserted into the slot in the wafer. The leaf gage and wafer assembly is positioned in the patient's mouth by the dentist. As the patient bites down on the leaf gage and wafer assembly the dentist marks the midline and most forward edge of the maxillary incisors on the upper surface of the wafer. The leaf gage and wafer assembly is then removed from the patient's mouth. The leaf gage is removed from the slot in the wafer and the wafer is reinserted into the patient's mouth exactly as before. That is, the dentist positions the wafer according to the midline and forward edge marks of the maxillary incisors. The patient is then instructed to bite firmly into the wafer. The wafer is made of a deformable material such that the wafer is contoured or bent at this time exactly like to occlusal plane of the patient's teeth. The wafer is then removed from the patient's mouth. The preselected portion of the leaf gage is reinserted into the wafer. The reassembled leaf gage and wafer assembly is then ready for use by the dentist in making the centric jaw relation record.

The present invention is useful in accurately recording the centric jaw relation on the dentulous patient. The minimum sufficient thickness of the leaf gage insures that no posterior prematurities of any teeth touch without causing excessive vertical separation of the opposing teeth. Once the prematurities are negated by this minimal separation of teeth, a wafer is used to make a centric relation record. Any suitable dental checkbite medium can be used with the wafer. A predetermined small quantity of the dental checkbite medium is distributed by the dentist over the upper and lower surfaces of the wafer. The dental checkbite medium extends from the upper surface to the lower surface of the wafer through the various apertures in the wafer to insure adherence of the dental checkbite medium to the wafer. The wafer and dental checkbite medium are then positioned in the patient's mouth, the patient is instructed to bite down and hold firmly onto the leaf gage and wafer assembly. The centric relation of the patient's teeth is recorded in the dental checkbite medium as the medium sets.

It is an object of this invention to provide an improved apparatus for assuring the precise location of a patient's mandible and for accurately recording that location.

It is a further object to provide an improved apparatus which is quick and easy to use correctly, pleasant to the patient while assisting the patient's retruded closure to the exact vertical dimension preselected by a dentist, and which requires minimal amounts of dental checkbite media.

It is also an object of this invention to provide an apparatus, for quickly making identical duplicate dental checkbit records for verification, which is usable with various types of recording media, and which apparatus is useful in most dentulous and partially edentulous situations; that is, where opposing upper and lower incisors remain.

The object and advantages of the invention will become apparent as the invention is described hereinafter in detail and with reference to the accompanying drawings.

DETAILED DESCRIPTION OF THE INVENTION

Figure 1:
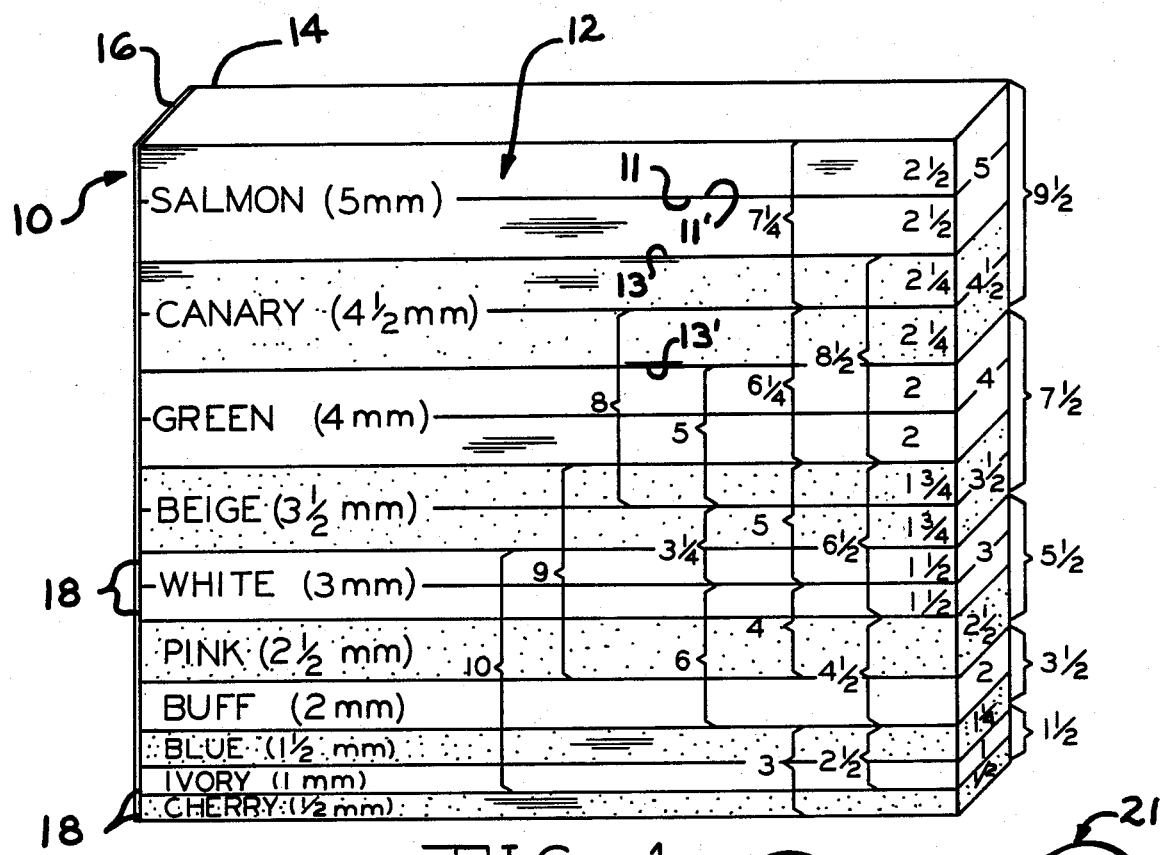
FIG. 1 is a diagrammatic view of a leaf gage booklet, showing various measured increments of leaves.
Figure 5:
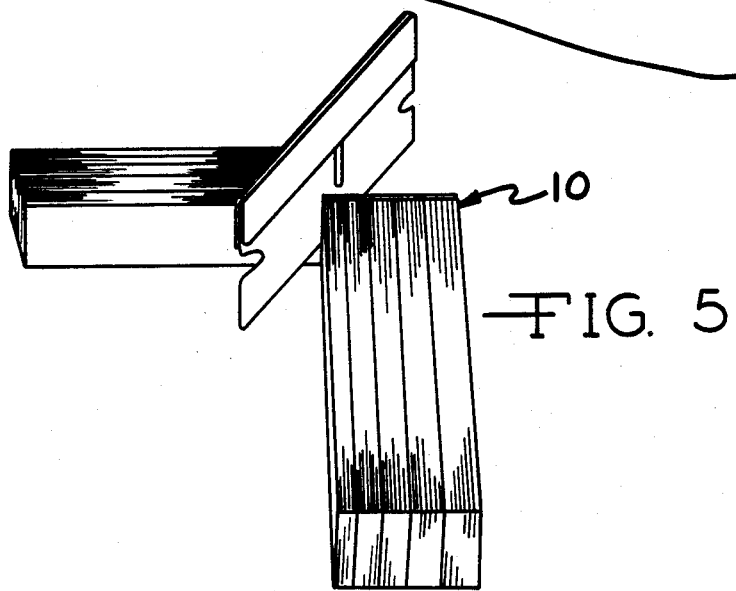
FIG. 5 is a perspective view of a leaf gage booklet being severed.
Figure 6:
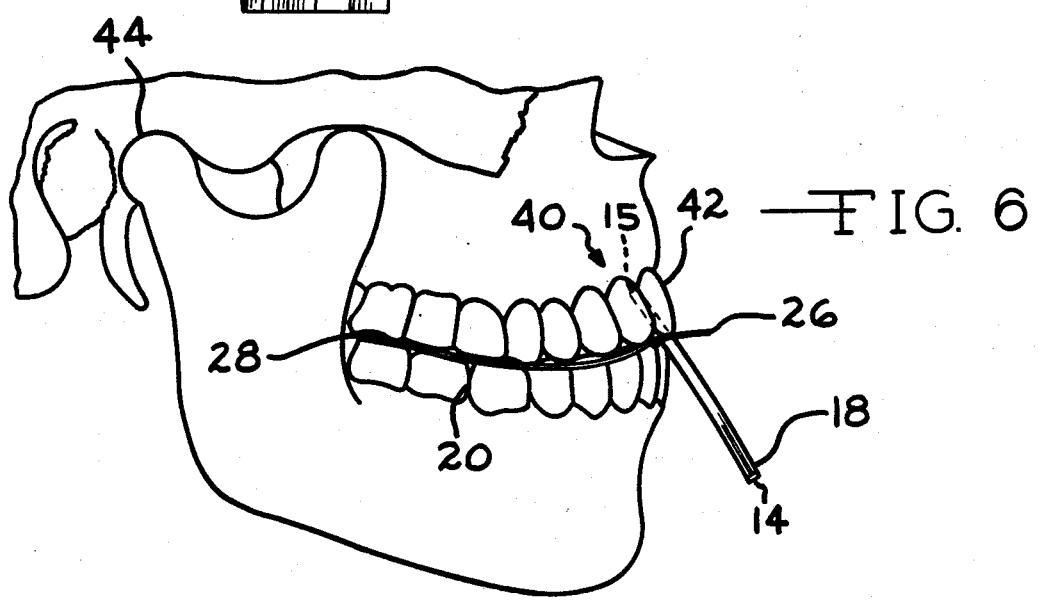
FIG. 6 is a diagrammatic view, partially in phantom, of a leaf gage and wafer positioned in a patient's jaw.

A diagrammatic view of a leaf gage booklet of the present invention is shown in FIG. 1. The leaf gage booklet 10 generally includes a plurality of leaves 12 made of a material such as a paper or a thin plastic. The leaves 12 have a bound end 14 and an unbound end 15. The leaves 12 are attached at the bound end 14 to a backing material 16. The backing material 16 can be made of a cheesecloth type of material and glue. A predetermined number of leaves 12 are grouped together in identifiable portions 18. Each portion 18 is made of a predetermined number of leaves which are dyed with edible or non-toxic dyes. Each of the differently colored portion 18 of the leaf gage booklet 10 represent a particular thickness. In the embodiment of the leaf gage booklet 10 shown in FIG. 1, the first or bottom portion 18 is 0.5 mm thick. Each succeeding portion 18, is an additional ½ mm thick, i.e., the second portion is 1 mm thick, the third portion is 1.5 mm thick, and so on until the top portion is 5 mm thick. As shown in FIG. 1, these portions 18 can be grouped together to allow for the selection of any desired thickness of leaf gage. The dentist can then determine which thickness of leaf gage is needed and separate those portions accordingly, as seen in FIG. 5, which shows a perspective view of a leaf gage booklet being severed. In the embodiment shown, the leaf gage portions 18 having thicknesses ranging from 3 mm through 5 mm have a substantially moisture impervious material, such as a coating of a thin sheet of the product known under the trademark MYLAR, on each of the adjacent leaves 11 and 11' in the middle or center of the leaf gage portion 18 such that the leaf gage portion 18 may be further divided into ½ of its particular thickness. For example, the leaf gage portion 18 having a thickness of 5 mm can be divided into equal portions of leaves each having a thickness of 2.5 mm thick. In another embodiment of the leaf gage (not shown) the leaf gage portions having thicknesses ranging from 3 mm through 5 mm can be divided into substantially equal portions by a center leaf of a different color. Further, in the embodiment shown, the first leaf 13 and last leaf 13' of each portion 18 are coated such that when the preselected portion 18 of the leaf gage booklet 10 is positioned within a patient's mouth, that portion 18 will not absorb any moisture. In another embodiment of the leaf gage (not shown) the leaves of the leaf gage portions are not coated with a sheeting. If the dentist so desires, a piece of adhesive tape, such as Scotch ® brand tape can be placed on the preslected leaf gage portion leaves that are contacted by the patient's teeth. The leaf gage booklet 10 is made of a disposable material so that the dentist will be able to use a new leaf gage portion 18 removed from a booklet 10 for each patient. If desired, the leaf gage booklet 10 of the present invention can be made from paper so that the leaf gage portions 18 do not have the spring or bounce that is normally associated with plastic leaf gages. When the patient bites down on the leaf gage portion 18, the leaf gage portion 18 is held in a tight position between the teeth of the patient and very little spring or bounce is present, thus enabling the dentist to accurately measure the occlusal relationship of the patient's teeth. In a preferred embodiment of the present invention, the width of the leaf gage booklet 10 ranges from approximately 8-9.5 mm and the length of the leaf gage booklet 10 ranges from approxmately 40-55 mm.

Figure 2:
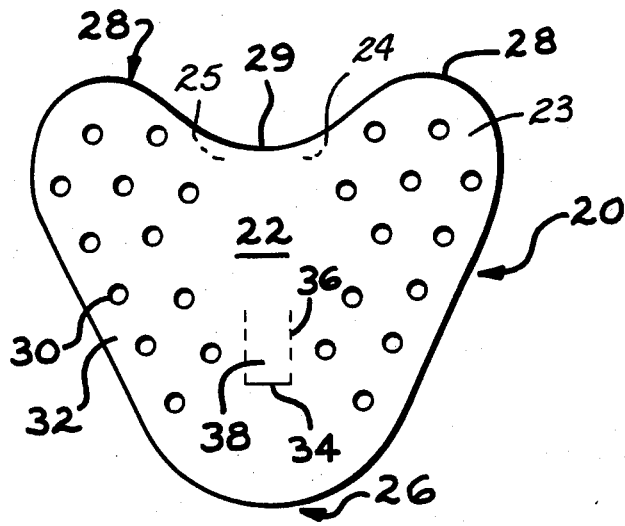
FIG. 2 is a plan view of one embodiment of a wafer.
Figure 3A:
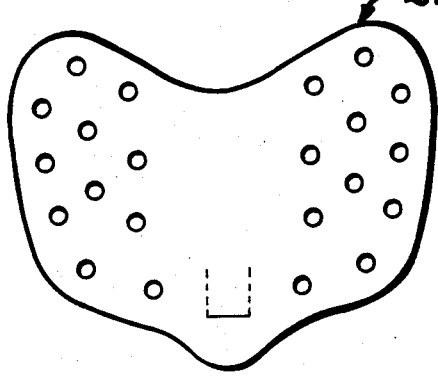
FIG. 3A is a plan view of still another embodiment of a wafer.
Figure 3:
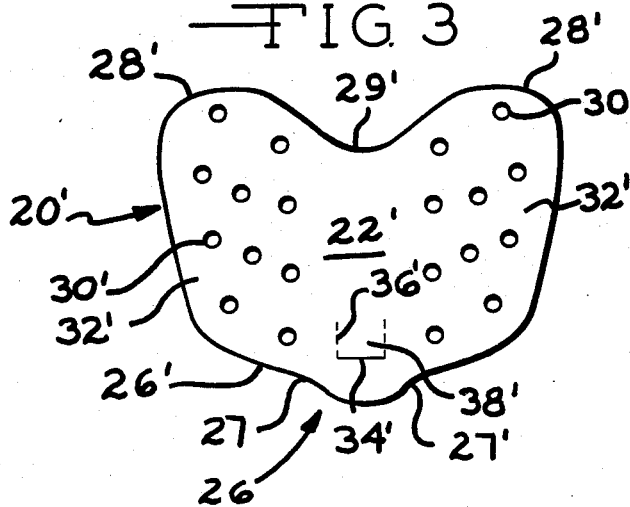
FIG. 3 is a plan view of an alternative embodiment of a wafer.
Figure 4:
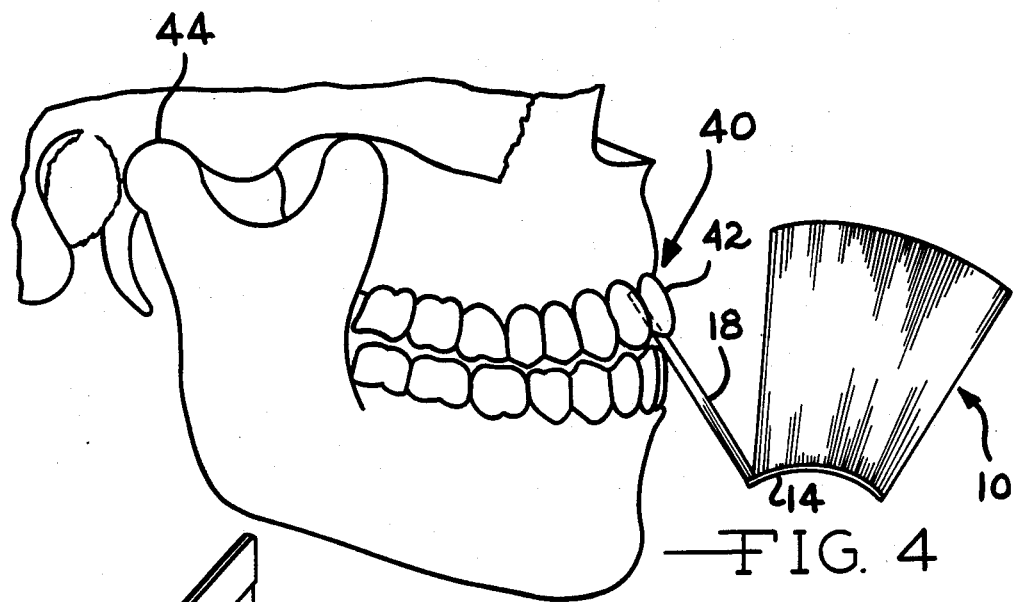
FIG. 4 is a diagrammatic view, partially in phantom, of a leaf gage positioned in a patient's jaw.
Figure 8A:
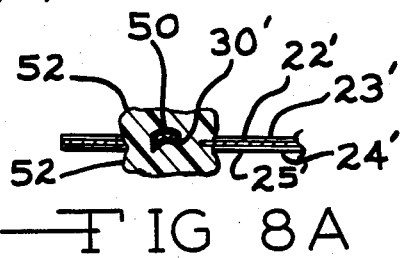
FIG. 8A is a view taken along line 8A—8A in FIG. 8, showing an exaggerated cross-sectional view of a portion of the wafer and dental checkbite medium.

Referring now to FIGS. 2-4, alternative embodiments of the wafer 20 of the present invention are shown. Referring now in particular to FIG. 2, the wafer 20 has a generally dental arcuate shape and is made of substantially rigid, yet vertically deformable material, such as a thin paper or plastic material. The wafer 20 can range in thickness from approximately 0.15 mm to 0.3 mm thick. The wafer 20 has a generally planar upper surface 22 and a planar lower surface 24. In the embodiment shown, the wafer 20 is made of a paper material and is coated on either or both surfaces 22 and 24 with a thin coating of a thin sheet 23 and 25, respectively, such as a 1.5 mil sheeting of the product known under the trademark MYLAR, as is shown in FIG. 8A. The sheets 23 and 25 on the wafer 20 aid in recording a bit impression made on the wafer 20 since the sheets 23 and 25 and the intervening deformable material of the wafer 20 help retain the peaks and valleys of the cusp of each tooth impression made on the wafer 20 by the patient's biting on the wafer 20, as will be described in detail below. While it is preferable to coat the surfaces of the wafer 20 such that the wafer 20 does not absorb moisture from the patient's mouth, most moisture contacts only the lower surface 24 and it is not necessary to coat the upper surface 22 of the wafer 20. Dental checkbite media, such as polyether rubber and other types of rubber will easily adhere to both the coated and uncoated surfaces of the wafer 20, as will be described in detail below.

The wafer 20 has a generally dental shape as shown in FIG. 2. The shape of the wafer 20 can be easily altered or trimmed by the dentist with scissors so that the wafer 20 easily fits the shape of the individual patient's mouth. The wafer 20 defines an anterior end 26 and a posterior end 28. The posterior end 28 defines a center portion 29 which curves anteriorly towards the anterior end 26 of the wafer 20. The anteriorly curved portion 29 of the wafer 20 prevents any gagging reflex of the patient when the wafer 20 is positioned in a patient's mouth. The wafer 20 includes a plurality of apertures 30 disposed along the wafer 20 and extending through the wafer 20. In a preferred embodiment, the apertures 30 are spaced apart at generally uniform intervals along the lateral edges 32 of the wafer 20. The location and number of apertures extending through the wafer can be varied such that various types of dental checkbite media which might require more surface area for bonding can be utilized with the wafer 20, as will be described in detail below. The wafer 20 further defines a slot 34 extending through the wafer 20. The slot 34 is positioned in substantially the center of the wafer 20 in spaced apart relationship to the anterior end 26 of the wafer 20. The slot 34 defines a series of perforations 36 which extend posteriorly from the slot 34. The perforations 36 extend through the wafer 20 such that the slot 34 and perforations 36 define a tab portion 38. The slot 34 and perforations 36 are separable from the wafer 20 such that the tab portion 38 can be bent at an acute angle downward from the plane of the wafer 20. The slot 34 has a length sufficient to receive a thick portion 18 of the leaf gage booklet 10 inserted into the slot 34.

An alternative embodiment of the wafer of the present invention is shown in FIG. 3, the wafer 20' has a smaller and wider arcuate shape. The shape of the wafer 20' can be easily altered or trimmed by the dentist so that the wafer 20' easily fits the shape of the individual patient's mouth. The wafer 20' has an anterior end 26' and a posterior end 28'. The posterior end 28' defines a center portion 29' which curves anteriorly towards the anterior end 26' of the wafer 20'. The anterior end 26' defines lateral portions 27 and 27' which curve posteriorly towards the posterior end 28'. The lateral curved portions 27 and 27' prevent any incisor interference with the wafer 20' when the patient has a deep vertical overlap of the opposing teeth. The wafer 20' includes a plurality of apertures 30' disposed along the wafer 20' and extending through the wafer 20'. In a preferred embodiment, the apertures 30' are spaced apart at generally uniform intervals along the lateral edges 32' of the wafer 20'. The location and number of apertures extending through the wafer can be varied such that various types of dental checkbite media which might require more surface area for bonding can be utilized with the wafer 20', as will be described in detail below. The wafer 20' further defines a slot 34' in extending through the wafer 20'. The slot 34' is positioned in substantially the center of the wafer 20' in spaced apart relationship to the anterior end 26' of the wafer 20'. The slot 34' defines a series of perforations 36' which extend posteriorly from the slot 34'. The perforations 36' extend through the wafer 20' such that the slot 34' and perforations 36' define a tab portion 38'. The slot 34' and perforations 36' are separable from the wafer 20 such that the tab portion 38' can be bent at an acute angle downward from the plane of the wafer 20'. The slot 34' has a length sufficient to receive a thick portion 18 of the leaf gage booklet 10 inserted into the slot 34'. Still another embodiment of the wafer of the present invention is shown in FIG. 3A. The wafer 21 has generally the same configuration as the wafer 20' shown in FIG. 3. The wafer 21 however, is slightly larger and wider in order to fit patients who have broader dental arches.

In order to use the leaf gage booklet 10 and wafer 20 of the present invention, the dentist visually examines the patient's mouth to determine approximately what size wafer and what portion of a leaf gage are necessary in order to obtain an accurate bit registration. Prior to making the dental centric relation registration, the dentist makes a determination of the minimum magnitude of incisor separation necessary by using a leaf gage to negate any existent posterior premature tooth contact that occurs during the mandibular terminal hinge arc of closure. When the dentist makes a centric relation recording, there is normally a 0.2 to 0.3 mm increased opening from the point of minimal magnitude of incisor separation. In most instances, the incisors will be apart 1-3 mm when the prematurely contacting teeth are barely separated. This degree of separation or vertical opening is necessary so that the proprioceptor nerves in the periodontal ligaments of the prematurely contacting teeth will not guide the mandible into the undesired centric occlusion postion. In situations of severe malocclusions and other relationships, it may be necessary to have an incisor opening of as much as 5-6 mm with a leaf gage to prevent posterior centric relation prematurities. Accurate centric relation recordings are possible only when there are no posterior tooth contacts or interferences. Some prior art methods, such as clutch frames, bite frames, face-bow forks, impression compound and hard portions of wax, produce undesirable interferences and usually necessitate an undesirably greater separation of the teeth (i.e., vertical jaw opening).

Referring now to FIG. 4, the patient's mouth 40 is generally shown. FIG. 4 is for illustration purposes, since the dentist would not necessarily keep the selected portion 18 attached to the leaf gage booklet 10 while using the selected portion 18 in the patient's mouth. The dentist separates out a predetermined portion 18 of a leaf gage booklet 10 and inserts the unbound end 15 of the selected leaf gage portion 18 into the patient's mouth. The patient is instructed to bite down with his incisors or front teeth 42 on the leaf gage portion 18. The patient is then asked whether any teeth are in contact with opposing teeth. If the patient feels any upper and lower teeth in contact the dentist must add additional leaves 12 or select a different and thicker portion 18 of the leaf gage booklet 10 to insert into the patient's mouth. The patient is then again instructed to bite down on the leaf gage portion 18. When the patient no longer feels any contact between his opposing teeth, the dentist instructs the patient to bite on the leaf gage portion 18 for a predetermined period of time. This period of time can be as long as 5 minutes. The patient bites on the leaf gage portion 18 so that the jaw and muscles surrounding the jaw naturally close the patient's mouth instead of having the nerve ending proprioceptors surrounding the teeth will not guide the jaw out of alignment, or into the undesired adaptive centric occlusion position. By biting on the leaf gage portion 18, the opposing teeth are not in contact with one another and the jaw muscles can retrude the jaw into a more natural position. The leaf gage portion 18 forms a tripod pressure point between the temporomandibular joints 44 of the jaw of the patient and the leaf gage portion 18. After the patient has maintained incisal pressure on the leaf gage portion 18 for the sufficient period of time, the patient is then instructed to open his mouth and the leaf gage portion 18 is removed. The dentist thus knows the exact thickness (color coded) of the leaf gage portion 18 on which the patient has bitten. The patient is then instructed to maintain his mouth in an open position and not to contact his upper teeth with his lower teeth. The dentist then uses this correct thickness leaf gage portion 18 to insert in the wafer for making the jaw relation record.

Figure 7:
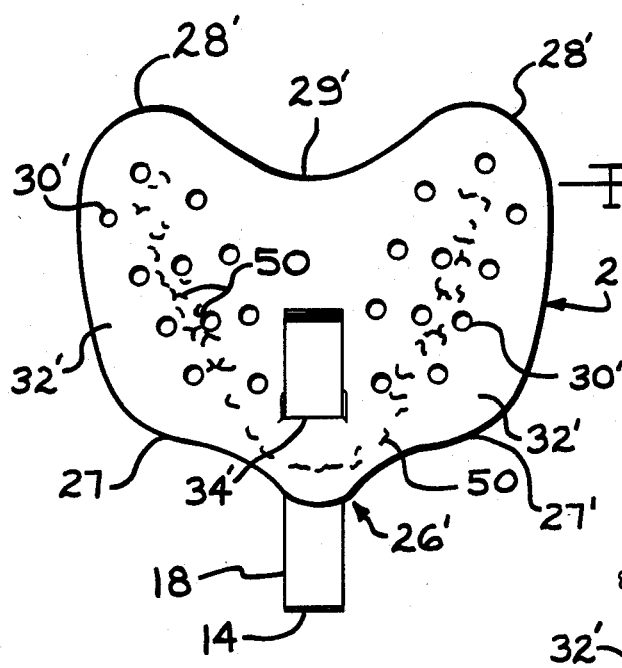
FIG. 7 is a plan view of a wafer and a portion of a leaf gage, showing a bit recording on the wafer made when the leaf gage portion was removed.

The dentist then selects a wafer 20' of the appropriate shape and thickness. If necessary the wafer 20' can be trimmed with scissors to more closely fit the shape of the patient's maxillary arch. The leaf gage portion 18 is inserted through the slot 34' and the perforations 36' in the wafer 20' so that the tab portion 38' is bent downward from the wafer 20'. The unbound end 15 of the leaf gage portion 18 extend upwardly and posteriorly through the plane of the wafer 20', as is shown in FIG. 7. The bound end 14 of the leaf gage portion 18 extends downwardly at an acute angle from the wafer 20'. The leaf gage portion 18 and the wafer 20' are inserted into the patient's mouth and the patient is instructed to bite down on the leaf gage portion 18 and wafer 20'. The leaf gage portion 18 and wafer 20' are positioned in the mouth so that the leaf gage portion 18 is centered at a 45° posterior upward slope between the incisors. The patient's head was first tipped backwards to stretch the supra and infrahyoid muscles as the patient is instructed to close his mouth and hold his teeth firmly on the leaf gage portion 18. The dentist marks the midline and labial extent of the maxillary incisors, and any excess lateral width or posterior length on the top surface 22' of the wafer 20'. The leaf gage portion 18 and wafer 20' are removed from the patient's mouth and the dentist trims any excess width or length off the wafer 20'. The dentist then removes the leaf gage portion 18 from the slot 34' in the wafer 20'. The wafer 20' is then reinserted into the patient's mouth and the dentist positions the wafer 20' according to the midline and labial extent of the maxillary incisors marks. The patient is then instructed to bite firmly into the wafer 20' for a predetermined time, generally between 5 to 10 seconds, to make upper and lower dental cusp impressions on the wafer 20'. The wafer 20' is thus conformed to the cuspal irregularities of the occlusal plane of the patient's mouth. The dentist then also determines from the tooth indentations the exact regions where the dental checkbite medium is to be applied onto the wafer 20'. The patient is instructed once again to lean back or tip the head back and keep the teeth apart or close gently with another leaf gage portion 18 or with a cotton roll (not shown) in place while the wafer 20' is prepared with a the dental checkbite medium 52.

Figure 8:
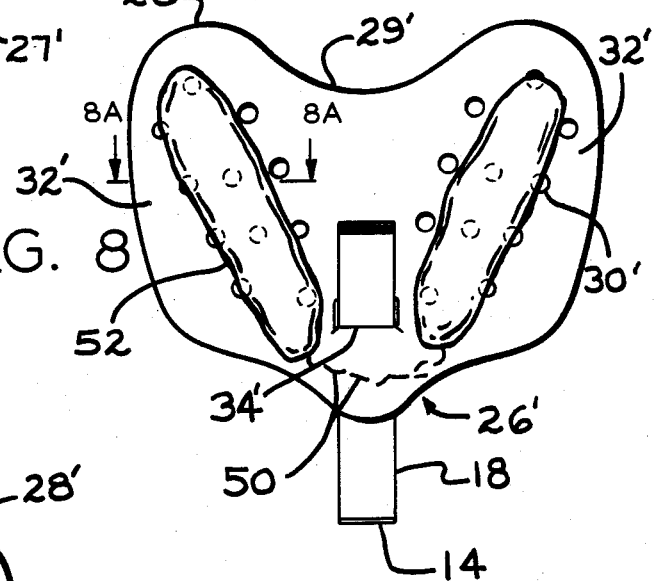
FIG. 8 is a plan view of a wafer and a portion of a leaf gage, showing a dental checkbite medium positioned on the wafer.

Referring now in particular to FIG. 7, the leaf gage portion 18 and wafer 20' are shown re-assembled for a checkbite after the wafer 20' was purposely deformed by the opposing upper and lower teeth. The wafer 20' has dental cusp indentations 50 where the patient has bitten down on the marked and centered wafer 20' with the leaf gage portion 18 removed therefrom. A small portion of the dental checkbite medium 52 is prepared by mixing, divided into four parts and applied adjacent each lateral edge 32' of both surfaces 22' and 24' of the wafer 20'. FIG. 8 shows the leaf gage portion 18 and wafer 20' with a dental checkbite medium 52 positioned on the wafer 20'. It is preferable that the dental checkbite medium 52 be positioned over the specific area where the teeth indentations 50 occurred and that only enough dental checkbite medium 52 be used to record the cusp tips. In that manner, an accurate jaw relation record will be made and subsequently used to correctly orient the dental casts on an articulator. FIG. 8A shows the position of the dental checkbite medium 52 on both the thin sheets 23' and 25' on the upper and lower surfaces 22' and 24' of the wafer 20'. The dental checkbite medium 52 extends through the apertures 30' such that the dental checkbite medium 52 positioned on the upper surface 22' adheres to the dental checkbite medium 52 positioned on the lower surface 24'. The wafer 20' is then quickly carried to the mouth, held by the bound edge 14 of the leaf gage and the edge 26' of the wafer 20', positioned according to the midline and incisal edge marks and the patient is instructed to close his jaw firmly so his incisors engage the leaf gage portion 18 as before and to hold his jaw firmly in this position. The wafer 20' was previously conformed to the irregularities of the occlusal plane of the patient's mouth so that the wafer 20' will not cause any deflection of the mandible as it closes in the terminal hinge position. Neither the leaf gage portion 18 nor the wafer 20' produce any posterior interference or undesired cuspal guidance while the dental checkbite medium 52 is setting. The thickness of the wafer 20' slightly over compensates for itself since the tab portion 38', which was bent downward at an acute angle from the plane of the wafer 20', in effect adds to the thickness of the leaf gage portion 18; that is, the lower incisors touch the tab portion 38' and the lingual surface of the patient's upper incisors touch the upper surface 22' of the wafer 20'. After the dental checkbite medium 52 has set, the leaf gage 18 and wafer 20' assembly is removed form the patient's mouth and the dental impresssion 54 is inspected for accuracy, necessary desired opposing tooth indentations and lack of any undesired opposing tooth contacts or penetration through the dental checkbite medium 52.

Figure 9A:
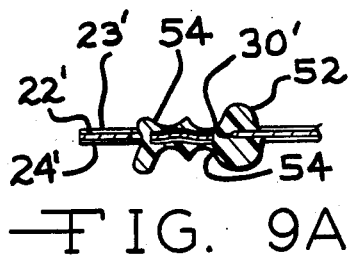
FIG. 9A is a view taken along the line 9A—9A in FIG. 9, showing an exaggerated cross-sectional view of a portion of the wafer and dental checkbite medium made with minimal separation of the opposing teeth.
Figure 9:
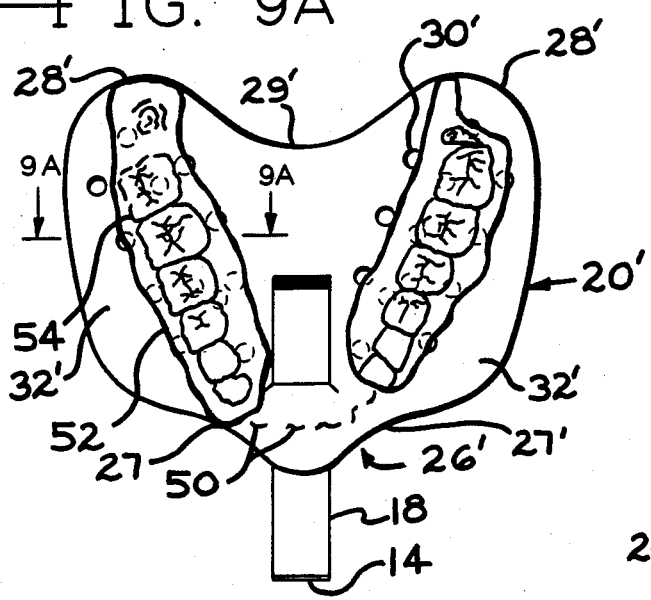
FIG. 9 is a plan view of a wafer and a portion of a leaf gage, showing a bite record made in a dental checkbite medium made with minimal separation of the opposing teeth.

FIG. 9 shows the leaf gage portion 18 and wafer 20' after a patient has made an appropriate retruded closure, causing cusp identations or dental impression 54 in the dental checkbite medium 52. The dental impression 54 is thus recorded in the dental checkbite medium 52. FIG. 9A shows the set dental checkbite medium 52 with the dental impression 54 recording on both the upper and lower surfaces 22' and 24' of the wafer 20'. The cusp impression 54 in the dental checkbite medium 52 thus shows the correcty oriented upper and lower occlusal surfaces of the patients teeth.

Figure 10:
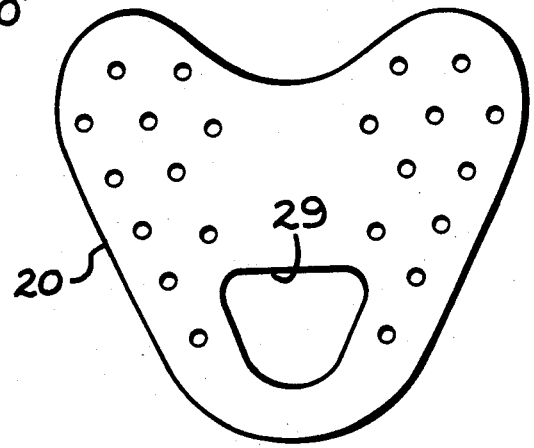
FIG. 10 is a plan view of the embodiment of the wafer shown in FIG. 2 having an opening extending therethrough.

The leaf gage and wafer of the present invention can be used quickly by the dentist to make duplicate centric relation checkbites by selecting the same shape wafer and the same thickness of leaf gage portion. The second wafer is trimmed and marked by the dentist exactly as the first wafer, inserted into the patient's mouth according to the marks, and the patient is instructed to bite firmly on the second wafer. Then, the dentist selects the same thickness color-coded leaf gage portion and inserts the leaf gage portion into the wafer. The dental checkbite medium is applied to the cuspal indented portions of the wafer, and the duplicate checkbite record is made as described above. Further, the leaf gage of the present invention can be used alone without the wafer for detection and correction of occlusal errors. Further, if the dentist determines it is necessary, several leaf gage portions of the correct thickness can be given to the patient for periodic use. As instructed by the dentist, the patient can place the leaf gage portion in the mouth at the correct angulation and bite on it firmly for short intervals of time to alleviate temporomandibular joint pain due to spasms of the superior heads of the lateral pterygoid muscles. The wafer of the present invention can be used for lateral and protrusive excursive records without a leaf gage, with the wafer being used as a dental checkbite medium carrying vehicle. As with the centric relation recording as described above, the wafer can be oriented in the patient's mouth and indented by the patient closing the teeth together with the jaw in the desired eccentric position, thus conforming the wafer to the irregulaties in the patient's occlusal plane and showing the dentist exactly where to apply the dental checkbite medium. An accurate excursive position (lateral or protruded) of the mandible is thus recorded with the wafer. The leaf gage and wafer assembly of the present invention can also be used for mounting the mandibular dental cast in the proper orientation to the upper dental cast on the dental articulator. The dentist or dental technician uses the patient's wafer with the leaf gage portion inserted therein to achieve the desired stability and accuracy while securing the two dental casts in their correct relationship while attaching them to the dental articulation with plaster. Further, as shown in FIG. 10, one embodiment of the wafer 20 can be altered such that an opening 29 is cut into substantially the center of the anterior end 26 of the wafer 20. The opening 29 allows the dentist to use the wafer 20 with a Lucia jig to guide the lower incisors and the mandible in an upward posterior direction.

The above detailed description of the present invention is given for explanatory purposes. It will be apparent to those skilled in the art that numerous changes and modifications can be made in the preferred embodiments of the invention described above without departing from the scope of the invention. Accordingly, the whole of the foregoing description is to be construed in an illustrative and not in a limitative sense, the scope of the invention being defined solely by the appended claims.

What I claim:

1. A dental apparatus for use by a dentist in obtaining an accurate centric relation record of the upper and lower teeth of a patient comprising:

a wafer having a generally arcuate shape and a size to permit positioning of said wafer in the patient's mouth between the upper and lower teeth, said wafer being made of a substantially rigid material which can be vertically deformed, said wafer having anterior and posterior ends, said wafer having upper and lower surfaces, such that when said wafer is positioned within the patient's mouth and the patient exerts occlusal pressure thereon said wafer is conformed to any irregularities of the occlusal plane of the patient's teeth and a dental impression of the patient's teeth is made on said upper and lower surfaces of said wafer;

said wafer further defining a slot for receiving a leaf gage portion, said slot being disposed adjacent said anterior end of said wafer and extending therethrough, such that when a first end of said leaf gage portion is inserted into said slot said leaf gage portion extends through said wafer in a posterior direction such that when the patient exerts occlusal pressure on said wafer, the patient's teeth also exert occlusal pressure on said leaf gage portion, whereby said leaf gage portion aids in positioning the patient's mandible in its most posterior position.

2. The dental apparatus of claim 1 wherein said posterior end of said wafer defines a central portion which curves anteriorly toward said anterior end of said wafer such that said central portion prevents the patient from exhibiting any choking reflex when said wafer is positioned within the patient's mouth.

3. The dental apparatus of claim 1, wherein said anterior end of said wafer defines at least one lateral portion which curves posteriorly toward said posterior end of said wafer such that said lateral portion prevents any incisor interference with said wafer when the patient is maintaining occlusal pressure on said wafer.

4. The dental apparatus of claim 1, wherein said slot in said wafer further includes opposing perforated portions which extend posteriorly from said slot, said opposing perforated portions being substantially perpendicular to said slot and substantially parallel to each other, said slot and said opposing perforated portions defining a tab portion of said wafer such that when said first end of said leaf gage portion is inserted through said slot said opposing perforated portions and said tab portion hold said leaf gage portions firmly in said slot in said wafer.

5. The apparatus of claim 1, wherein said wafer further defines a plurality of spaced apart apertures disposed along said wafer and extending therethrough such that when a dental checkbite medium is deposited on said upper and lower surfaces of said wafer said dental checkbite medium extends through at least several said apertures and said dental checkbite medium deposited on said upper surface contacts said dental checkbite medium deposited on said lower surface and adheres to said dental checkbite medium on said lower surface thereby holding said checkbite medium together by connection through said apertures.

6. The apparatus of claim 1, wherein said wafer is made of a paper material.

7. The apparatus of claim 1, wherein at least one surface of said wafer is coated with a thin moisture impervious material such that said wafer does not absorb moisture when said wafer is positioned in the patient's mouth and will retain cuspal deformed indentations.

8. The apparatus of claim 1, wherein said leaf gage portion is affixed at a second end to a plurality of other leaf gage portions to form a booklet, said booklet being composed of said plurality of said leaf gage portions, each of said leaf gage portions having a predetermined thickness, said booklet being divisible into predetermined measurable leaf gage portions, such that a predetermined thickness of said booklet can be inserted into said slot of said wafer.

9. The apparatus of claim 8, wherein each of said predetermined measurable leaf gage portions of said leaf gage booklet are color-coded such that each predetermined thickness of said leaf gage portion is readily identifiable from other said leaf gage portions.

10. The apparatus of claim 9, wherein at least one of said colored leaf gage portions further includes a center leaf of a different color, such that the center of said leaf gage portion is easily identifiable so that said leaf gage portion can be further divided into sections of substantially equal thicknesses.

11. The apparatus of claim 8, wherein said leaf gage portion is made of a paper material.

12. The apparatus of claim 8, wherein each of said leaf gage portions includes a plurality of leaves, each of said leaves affixed at said second end to form said leaf gage portion, each of said leaf gage portions further having a first leaf and a last leaf, said first and last leaves being coated with a substantially moisture impervious material such that when said leaf gage portion is positioned in the patient's mouth, said leaf gage portion does not absorb moisture.

13. The apparatus claim 12, wherein at least one of said leaf gage portions further includes adjacent leaves in the center of said leaf gage portion having a coating thereon, such that the center of said leaf gage portion is easily identifiable so that said leaf gage portion can be further divided into sections of substantially equal thicknesses.

* * * * *